(12) United States Patent
Duan et al.

(10) Patent No.: US 11,149,257 B2
(45) Date of Patent: Oct. 19, 2021

(54) ASCORBATE PEROXIDASE MUTANT MAAPXI-M36K AND APPLICATION THEREOF

(71) Applicant: South China Botanical Garden, Chinese Academy of Sciences, Guangzhou (CN)

(72) Inventors: Xuewu Duan, Guangzhou (CN); Lu Xiao, Guangzhou (CN); Guoxiang Jiang, Guangzhou (CN); Yueming Jiang, Guangzhou (CN); Huiling Yan, Guangzhou (CN); Zhiwei Li, Guangzhou (CN); Jing Zeng, Guangzhou (CN); Xiaochun Ding, Guangzhou (CN)

(73) Assignee: SOUTH CHINA BOTANICAL GARDEN, CHINESE ACADEMY OF SCIENCES, Guangzhou (CN)

( * ) Notice: Subject to any disclaimer, the term of this patent is extended or adjusted under 35 U.S.C. 154(b) by 45 days.

(21) Appl. No.: 16/722,238

(22) Filed: Dec. 20, 2019

(65) Prior Publication Data
US 2020/0354691 A1    Nov. 12, 2020

(30) Foreign Application Priority Data

May 10, 2019   (CN) .......................... 201910388128.2

(51) Int. Cl.
| | | |
|---|---|---|
| *C12N 9/02* | (2006.01) | |
| *C12N 15/52* | (2006.01) | |
| *C12N 15/70* | (2006.01) | |

(52) U.S. Cl.
CPC ........... *C12N 9/0004* (2013.01); *C12N 15/52* (2013.01); *C12N 15/70* (2013.01); *C12Y 111/01011* (2013.01)

(58) Field of Classification Search
CPC ...... C12N 9/0004; C12N 15/52; C12N 15/70; C12N 9/0065; C12Y 111/01011
See application file for complete search history.

*Primary Examiner* — Iqbal H Chowdhury
(74) *Attorney, Agent, or Firm* — Tutunjian & Bitetto, P.C.

(57) ABSTRACT

The present invention provides an ascorbate peroxidase mutant MaAPX1$^{M36K}$ and an application thereof, belonging to the technical field of biotechnology. An amino acid sequence of the mutant MaAPX1$^{M36K}$ of the present invention is shown in SEQ ID NO. 3. In the present invention, the mutant MaAPX1$^{M36K}$ reconstruction protein is obtained by the method of prokaryotic expression. It is found that the mutant MaAPX1$^{M36K}$ improves catalytic efficiency by nearly 5 times, providing a technical reference for further study and application of APX1.

2 Claims, 2 Drawing Sheets
Specification includes a Sequence Listing.

ASCORBATE PEROXIDASE MUTANT MAAPXI-M36K AND APPLICATION THEREOF

CROSS REFERENCE TO RELATED APPLICATIONS

This application claims priority to Chinese Application No. 201910388128.2, filed on May 10, 2019, entitled ASCORBATE PEROXIDASE MUTANT MaAPX1$^{M36K}$ AND APPLICATION THEREOF.

Further, this patent application incorporates by reference the Sequence Listing file enclosed herewith having the file name "SEQ.LISTING_ST25.txt" which is comprised of 7 kilobytes and has a date of creation of Nov. 22, 2019

TECHNICAL FIELD

The present invention belongs to the technical field of biotechnology, and particularly relates to an ascorbate peroxidase mutant MaAPX1$^{M36K}$ and an application thereof.

BACKGROUND

As a by-product of cell metabolism, Reactive Oxygen Species (ROS) mainly includes $H_2O_2$, superoxide anion, singlet oxygen, etc., and plays an important role in signal transduction and state stabilization. However, when subjected to environmental stress or during aging, excessive accumulation of ROS will cause oxidative damage to proteins, DNA, lipids and other macromolecules, thus resulting in loss of structure and function, even cell death. To resist oxidative stress, a complex protection system is biologically evolved, e.g., ROS scavenger enzyme and macromolecular repairing system.

There are some antioxidant enzyme systems in plants, such as superoxide dismutase, ascorbate peroxidase (APX), catalase, glutathione peroxidase, peroxidase; additionally, there are some low molecular weight (LMW) antioxidants, such as VC, glutathione, tocopherol and phenolic compound. APX has higher affinity to $H_2O_2$, generally, VC serves as an electron carrier to catalyze $H_2O_2$ to decompose into oxygen and water, which plays an important role in clearing away $H_2O_2$ in chloroplast, mitochondria, cytoplasm, peroxysome and apoplast. APX activity in plants is affected by various post-translation modifications, but there is little related report in regard to how to improve the APX activity.

SUMMARY

In view of this, an objective of the present invention provides an ascorbate peroxidase mutant MaAPX1$^{M36K}$ and application thereof. The present invention changes the hydrophobicity in the center of the ascorbate peroxidase activity, improving the activity of ascorbate peroxidase by nearly 5 times.

In order to achieve the foregoing invention objective, the present invention provides the following technical solutions:

The present invention provides an ascorbate peroxidase mutant MaAPX1$^{M36K}$, where an amino acid sequence of the mutant MaAPX1$^{M36K}$ is shown in SEQ ID NO.3.

The present invention further provides a construction method of a ascorbate peroxidase mutant MaAPX1$^{M36K}$ gene, the mutant MaAPX1$^{M36K}$ gene is obtained by a PCR method, a primer for the PCR includes a primer pair containing a restriction site and a primer pair containing a mutation site; a sequence of the primer pair containing the restriction site is shown in SEQ ID NO.4-5; a sequence of the primer pair containing the mutation site is shown in SEQ ID NO.6-7.

Preferably, the restriction site is a restriction site of an incision enzyme nde I.

Preferably, the PCR method includes: (1) MaAPX1 gene serves as a template, and sequences shown in SEQ ID NO.4 and SEQ ID NO.7 serve as primers for PCR to obtain a first PCR product;

(2) MaAPX1 gene serves as a template, and sequences shown in SEQ ID NO.5 and SEQ ID NO.6 serve as primers for PCR to obtain a second PCR product;

(3) The first PCR product and the second PCR product serve as templates, and sequences shown in SEQ ID NO.4-5 serve as primers for PCR to obtain a PCR product of the mutant MaAPX1$^{M36K}$ containing the restriction site; where there is no time order between steps (1) and (2).

Preferably, the PCR procedures in steps (1)-(3) are independently as follows: pre-degenerated for 4 min at 94° C.; degenerated for 30 s at 94° C., annealed for 30 s at 60° C. and extended for 90 s at 72° C. for 35 cycles; extended for 10 min at 72° C.

The present invention further provides a recombinant expression plasmid including the mutant MaAPX1$^{M36K}$, and a construction method of the recombinant expression plasmid including a step of ligating the mutant MaAPX1$^{M36K}$ gene with an expression vector pET28a(+).

The present invention further provides a cell line for expressing the mutant MaAPX1$^{M36K}$ or the mutant MaAPX1$^{M36K}$ gene obtained by the construction method or the recombinant expression plasmid, and the cell line expresses cells with *Escherichia coli* as a host.

The present invention further provides an application of the mutant MaAPX1$^{M36K}$ or the mutant MaAPX1$^{M36K}$ gene obtained by the construction method or the recombinant expression plasmid or the cell line in improving the activity of ascorbate peroxidase.

The present invention provides an ascorbate peroxidase mutant MaAPX1$^{M36K}$, and an amino acid sequence of the mutant MaAPX1$^{M36K}$ is shown in SEQ ID NO.3. In the present invention, the mutant MaAPX1$^{M36K}$ is obtained by performing site-directed mutation on the amino acid sequence shown in SEQ ID NO.2 to mutate Met on the 36th site into Lys, thus improving the activity of ascorbate peroxidase. The ascorbate peroxidase mutant MaAPX1$^{M36K}$ obtained by the present invention may serve as a mutant material capable of significantly enhancing enzyme catalytic activity, thus providing reference for further study of APX.

DETAILED DESCRIPTION

Figure 1:
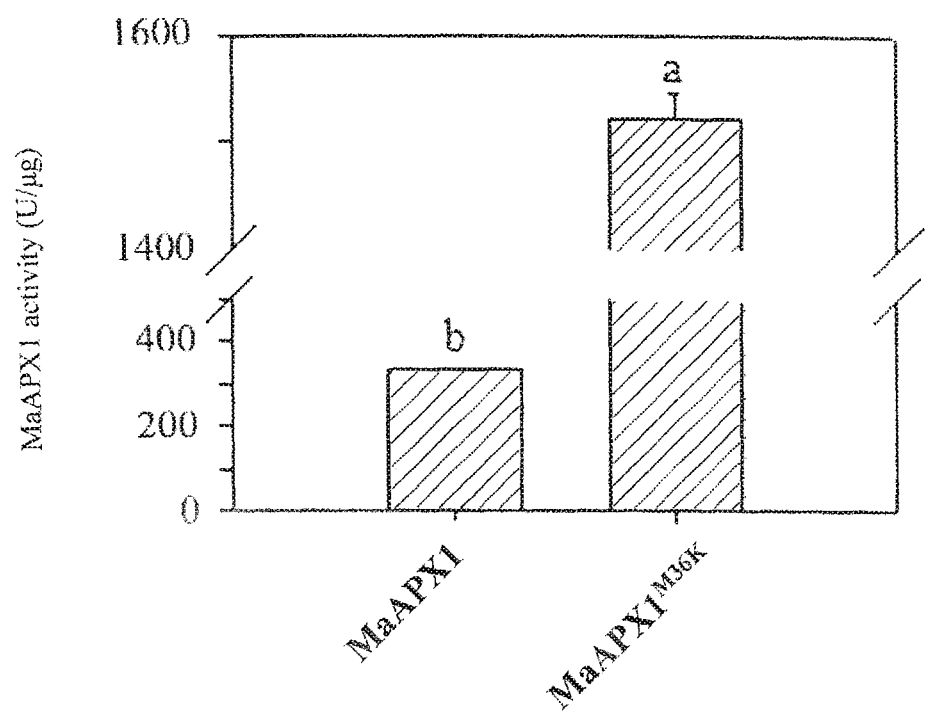
FIG. 1 is a comparison diagram showing enzyme activity measured by spectrophotometry in embodiments of the present invention.

The present invention provides an ascorbate peroxidase mutant MaAPX1$^{M36K}$, and an amino acid sequence of the mutant MaAPX1$^{M36K}$ is shown in SEQ ID NO.3. The mutant MaAPX1$^{M36K}$ of the present invention is preferably to mutate Met on the 36th site into Lys;

the amino acid sequence of the MaAPX1 is shown in SEQ ID NO.2. There is no special limitation to the method of the mutation in the present invention, preferably site-directed mutagenesis is taken. MaAPX1 of the present invention is preferably from banana, and its gene sequence is shown in SEQ ID NO.1; there are 750 base sequences in total, the protein coded by the gene contains 249 amino acids, corresponding to GSMUA_Achr5T07280_001 in banana genome.

The present invention further provides a construction method of a ascorbate peroxidase mutant MaAPX1$^{M36K}$ gene, the mutant MaAPX1$^{M36K}$ gene is obtained by a PCR method, a primer for the PCR includes a primer pair containing a restriction site and a primer pair containing a mutation site; a sequence of the primer pair containing the restriction site is shown in SEQ ID NO.4-5; a sequence of the primer pair containing the mutation site is shown in SEQ ID NO.6-7.

The mutant MaAPX1$^{M36K}$ gene of the present invention is preferably obtained by a PCR method, and the PCR primer includes a primer pair containing a restriction site and a primer pair containing a mutation site, specifically as shown in Table 1:

TABLE 1

Primers demanded for cloning MaAPX1 and MaAPX1$^{M36K}$ genes

|  | Primer name | SEQ ID NO | Sequence |
| --- | --- | --- | --- |
| Primer containing the restriction site | Forward primer | 4 | CCGCGCGGCAGCCATATGGCGA AGTCGTATCCGACGGTGA |
|  | Reverse primer | 5 | AGTCATGCTAGCCATATGTTAAG CCTCAGCAAATCCGAGTTCT |
| Primer containing the mutation site | Forward primer | 6 | AACTGTGCCCCGTTG<u>AAG</u>CTCC GGCTC |
|  | Reverse primer | 7 | GAGCCGGAG<u>CTT</u>CAACGGGGC ACAGTT |

The mutation site is located in the underlined portion of the sequence of the primer containing the mutation site in Table 1.

The restriction site of the present invention is preferably a restriction site of an incision enzyme nde I.

In the present invention, the above primer is used for PCR cloning of the mutant MaAPX1$^{M36K}$ gene, and the PCR cloning preferably includes:

(1) MaAPX1 gene serves as a template, and sequences shown in SEQ ID NO.4 and SEQ ID NO.7 serve as primers for PCR to obtain a first PCR product;

(2) MaAPX1 gene serves as a template, and sequences shown in SEQ ID NO.5 and SEQ ID NO.6 serve as primers for PCR to obtain a second PCR product;

(3) The first PCR product and the second PCR product serve as templates, and sequences shown in SEQ ID NO.4-5 serve as primers for PCR to obtain a PCR product of the mutant MaAPX1$^{M36K}$ containing the restriction site; where there is no time order between steps (1) and (2).

In the PCR method of the present invention, the PCR procedures in steps (1)-(3) are independently as follows: pre-degenerated for 4 min at 94° C.; degenerated for 30 s at 94° C., annealed for 30 s at 60° C. and extended for 90 s at 72° C. for 35 cycles; extended for 10 min at 72° C. There is no special definition in the PCR system of the present invention as long as a conventional PCR system is taken available.

After obtaining the mutant MaAPX1$^{M36K}$ gene, the present invention preferably further includes electrophoresis detection, and there is no special limitation to the electrophoresis detection as long as a conventional agarose gel electrophoresis is available.

The present invention further provides a recombinant expression plasmid including the mutant MaAPX1$^{M36K}$, and the construction method of a recombinant expression plasmid includes a step of ligating the mutant MaAPX1$^{M36K}$ gene with an expression vector pET28a(+).

In the present invention, the obtained mutant MaAPX1$^{M36K}$ gene is ligated with the expression vector pET28a(+), and a reaction system for the ligation of the present invention is an In-fusion reaction system (TaKaRa): preferably purified RCR fragment, 100 ng; Linearized vector, 200 ng; 5×In-Fusion HD Enzyme Premix, 2 μL, replenishdeionized waterup to 10 μL in total volume. A corresponding negative control: Linearized vector, 1 μL; 5× In-Fusion HDEnzyme Premix, 2 μl; Deionized water, 7 μL. A pUC19 positive control: purified RCR fragment, 2 μL of 2 kb control insert; Linearized vector: pUC19control vector, 1 μL; 5× In-Fusion HD Enzyme Premix, 2 μL; deionized water: 5 μL. In the present invention, the ligation procedure is preferably as follows: the above reaction system is slightly mixed and incubated at 50° C. for 15 min., and then put the reaction system on ice to obtain a ligation product. The ligation product can be used for further transformation or stored at −20° C.

The present invention further provides a cell line for expressing the mutant MaAPX1$^{M36K}$ or the mutant MaAPX1$^{M36K}$ gene obtained by the construction method or the recombinant expression plasmid, and the cell line expresses cells with *Escherichia coli* as a host. In the present invention, the cell line expresses the mutant MaAPX1$^{M36K}$ using pET28a(+) as a vector and using the *Escherichia coli* BL21(DE3) as a host. In the present invention, the cell line is preferably obtained by the following steps: the recombinant expression plasmid serves to transform *Escherichia coli* DH5a competent cells, and it is cultured in liquid LB medium for 1 h (37° C., 200 rpm), partial bacteria solution is coated on a solid LB plate (containing 1 μg/mL kanamycin) and then cultured in constant temperature incubator (37° C.) for overnight.

Positive colonies are picked for PCR identification and sequencing identification. The correctly-sequenced plasmid serves to transform *Escherichia coli* BL21(DE3) competent cells, and the positive bacterial solution is identified by PCR and stored at −80° C. by adding 50% sterilized glycerol in 1:1 volume to obtain the cell line. There is no special limitation to the sequencing identification of the present invention, preferably it is conducted by a biotechnology company. In embodiments of the present invention, the sequencing is conducted by Guangzhou IGE Biotechnology Company. In the present invention, the liquid LB medium includes following ingredients: peptone, 10 g/L; yeast powder, 5 g/L; sodium chloride, 10 g/L,pH7.0; the solid LB medium includes the following ingredients: peptone, 10 g/L; yeast powder, 5 g/L; sodium chloride, 10 g/L; agar powder, 1.5%, pH 7.0.

The present invention further provides an application of the mutant MaAPX1$^{M36K}$ or the mutant MaAPX1$^{M36K}$ gene obtained by the construction method or the recombinant expression plasmid or the cell line in improving the activity of ascorbate peroxidase.

The ascorbate peroxidase mutant MaAPX1$^{M36K}$ and the application thereof provided by the present invention will be described in detail with reference to embodiments below. However, these embodiments should not be construed as limiting the protection scope of the present invention.

Embodiment 1

1. Sampling: the selected banana (Musa spp., AAA group cultivar "Brazil") fruit were harvested from an orchard in Nansha, Guangzhou city, Guangdong Province, China.

2. MaAPX1 Gene Cloning

Total RNA was extracted from banana pericarp using the conventional hot borate method. The extracted total RNA was reversely transcribed into cDNA using the method provided by a kit PrimeScript™ RT Master Mix(Perfect Real Time, RR036A, TaKaRa). The reaction system includes: RNA(<500 ng), X µL; 5× Mix, 2 µL; RNase free water, Y µL; 10 µL in total volume. The mixed reaction system was incubated in thermostatic water bath (37° C.) for 15 min, then heated in metal bath (85° C.) for 5 s, and finally cooled on ice.

3. Construction of MaAPX1 Expression Strain

Primers, which containing nde I restriction site and mutation site, were designed according to the MaAPX1 gene sequence from Banana Genome Hub. The primer sequences were shown in Table 1.

The forward primer containing the restriction site and the reverse primer containing the mutation site respectively served for PCR to obtain a product 1, then the forward primer of the mutation site and the reverse primer of the restriction site served for PCR to obtain a product 2. Products 1 and 2 served as templates, forward and reverse primers containing the restriction site served for PCR to obtain a mutant MaAPX1$^{M36K}$ PCR product. The PCR conditions are as follows: pre-degenerated for 4 min at 94° C.; degenerated for 30 s at 94° C., annealed for 30s at 60° C. and extended for 90 s at 72° C. for 35 cycles; extended for 10 min at 72° C. At the end of PCR reaction, it was detected by 1% agarose gel electrophoresis.

The PCR product of MaAPX1$^{M36K}$ was collected and ligated with pET28a(+) vector to construct a recombinant expression plasmid. Then the recombinant expression plasmid was transformed Escherichia coli DH5a competent cells and cultured in liquid LB medium for 1 h (37° C. 200 rpm). Partical bacteria solution was coated on solid LB plate (containing 1 µg/mL kanamycin) and cultured for overnight at 37° C. Positive colonies were picked for PCR identification, and of which sequence was identified by Guangzhou IGE Biotechnology Company.

The correctly-sequenced plasmid, which was sent back by the company, was transformed Escherichia coli BL21(DE3) competent cells. The positive bacterial solution was identified by PCR and stored at −80° C. by adding 50% sterilized glycerol in 1:1 volume.

4. Prokaryotic Expression and Purification of MaAPX1 and MaAPX1$^{M36K}$ (1) Prokaryotic Expression Enlarge cultivation (37° C., 200 rpm) was performed to the strain, until the concentration of the bacteria solution was up to OD600 (0.4-0.6). The bacteria solution was cooled to 16° C., then added protein inducer IPTG with a final concentration of 1 mM for low temperature induction. The bacteria solution was cultured at 16° C. at 100 rpm for 20-24 h and collected the thalli by centrifuging.

(2) Protein Purification

The collected thalli was suspended with sterile water and removed the LB medium by centrifuging (4° C., 6000 g) for 8 min. Suspending the thalli with protein extracting solution (20 mM Tris-HCl, 500 mM NaCl, pH 7.5) and adding Triton-100 into the suspension in a volume of 1:1000 to improve the protein extraction efficiency. The thalli were broken for 1 h (ultrasound for 30s, stop for 30s) by a low-temperature and ultrahigh-pressure continuous flow cell crusher. During ultrasonication process, the bacteria solution should be kept in an ice bath fully to avoid protein activity being affected caused by probe heating. PMSF was then added into the bacteria solution with a final concentration of 1 mM to inhibit the protein degradation. Centrifuging the bacteria solution and collecting the supernatant, and then filtered the supernatant with membrane(0.45 µm). The Ni-NTA agarose (Ni-NTASuperflow Cartridges, QIAGEN), which was balanced with protein extracting solution, was added into protein solution. And then, the protein solution was added with imidazole for a final concentration of 10 mM to make the protein rotating combination with the Ni-NTA agarose for more than 2 h at 4° C.

The protein supernatant together with Ni-NTA agarose was transferred into the nickel column. After the supernatant flowed through the nickel column completely, 40 mM imidazole solution (containing 20 mM Tris-HCl, 500 mM NaCl, pH 7.5) was used to wash impure proteins until there was no protein in the flowing solution analysis by Coomassie brilliant blue (CBB) G250 (Beyotime). The target protein was eluted by using 250 mM imidazole (containing 20 mM Tris-HCl, 500 mM NaCl, pH 7.5). The collected target protein solution should be desalted timely by centrifuging (4° C., 3800 g) using desalination column (Sephadex G-25, GE),with potassium phosphate buffer solution (50 mM pH 7.0) to displace imidazole. The purified target protein was analyzed and stored at −80° C.

5. MaAPX1 and its mutant MaAPX1$^{M36K}$ activity were analyzed by spectrophotometry and reactive staining, and the method was as follows:

Spectrophotometry

The solvent of purified protein was displaced with 50 mM pH 7.0 potassium phosphate buffer solution (containing 0.1 mM EDTA-Na2). The activity was measured as follows:

(1) The protein was diluted to certain concentration and measured by a microplate reader according to the instructions of BCA kit (Beyotime).

(2) The wavelength of ultraviolet spectrophotometer was set at 290 nm. 1 mL quartz cuvette was selected and 50 mM pH7.0 potassium phosphate buffer solution (containing 0.1 mM EDTA-Na 2) served as a control group. Firstly, 500 µL protein solution and 250 µL 1 mM VC solution (50 mM pH7.0 potassium phosphate buffer solution, 0.1 mM EDTA-Na2) were added into the cuvette and mixed well. The reaction was initiated by adding 250 µL 0.12 M $H_2O_2$. The change of OD values within 2 min was recorded. Enzyme activity (U) was defined as the amount of enzymes which can oxidize 1 μM VC every minute (25° C.). Three repeats for each experiment.

The protein activity was calculated as follows:

APX activity $U=(\Delta OD \times 1000 \times 1000)/(t \times c \times v \times 2.8)$;

ΔOD: change of absorbance value;

1000: mL was converted to μL;

1000: mmol was converted to μmol;

t: time, min;

c: protein concentration, mol/L;

v: protein volume, mL;

2.8: absorptivity, mmol/L cm.

The results were shown in FIG. 1, the MaAPX1 activity was (335.85±0.52)U/μg, the mutant MaAPX1$^{M36K}$ activity was (1522.11±22.9)U/μg.

Reactive Staining

Specific steps were as follows:

(1) Non-Denatured Gel

The formula of a separation gel (10%, 15 mL) was shown in Table 2:

TABLE 2

Formula of the separation gel

| Reagent | Dosage (mL) |
| --- | --- |
| H$_2$O | 6.00 |
| 30% Polyacrylamide | 5.00 |
| 1.5M Tris-HCl pH 8.8 | 3.80 |
| 10% Ammonium persulfate | 0.15 |
| 1M VC | 0.04 |
| TEMED | 0.01 |

The formula of a spacer gel (4 mL) was shown in Table 3:

TABLE 3

Formula of the spacer gel

| Reagent | Dosage (mL) |
| --- | --- |
| H$_2$O | 2.75 |
| 30% Polyacrylamide | 0.65 |
| 1M Tris-HCl pH 6.8 | 0.50 |
| 10% Ammonium persulfate | 0.04 |
| 1M VC | 0.005 |
| TEMED | 0.005 |

(2) The Formula of an Electrophoresis Solution (1 L) was Shown in Table 4:

TABLE 4

Formula of the electrophoresis solution

| Reagent | Dosage (g) |
| --- | --- |
| Tris | 3.0 |
| Glycine | 14.4 |
| VC | 3.5 |

Configuration of the denatured gel and electrophoresis solution was prepared according to TaKaRa formula available.

(3) 5× Loading Buffer

The formula of a non-denatured 5× loading buffer was shown in Table 5:

TABLE 5

Formula of the non-denatured 5 × loading buffer

| Reagent | Dosage |
| --- | --- |
| 0.5M Tris-HCl pH 6.8 | 2.5 mL |
| Bromophenol blue | 0.025 g |
| Glycerin | 2.5 mL |
| 400 Mm VC | 0.01 mL |

The formula of a denatured 5× loading buffer was shown in Table 6:

TABLE 6

Formula of the denatured 5 × loading buffer

| Reagent | Dosage |
| --- | --- |
| 0.5M Tris-HCl pH 6.8 | 2.5 mL |
| Bromophenol blue | 0.025 g |
| Glycerin | 2.5 mL |
| SDS | 0-5 g |
| DTT | 0-39 g |

(4) The protein concentration was determined by BCA method. The protein was quantified by running denatured gel and the enzyme activity was analyzed by running non-denatured gel. Before loading samples, corresponding loading buffers were added respectively. The samples for running denatured gel were needed to be boiled for 10 min to denaturize the protein, and then centrifuged for 10 min (25° C., 12000 rpm). During the process of non-denatured gel electrophoresis, the electrophoresis tank should be placed in refrigerator (4° C., avoid light) to protect the protein samples from denaturing due to the rising temperature of the electrophoresis solution. Electrophoresis conditions: run the spacer gel at a constant pressure of 100V, then switched to 120 V for running separation gel.

(5) At the end of electrophoresis, the denatured gel was stained with CBB solution for 4-5 h, and then decolored and captured. The non-denatured gel was washed with sterile water and then immersed in equilibrium liquid (50 mM pH 7.0 potassium phosphate buffer solution, containing 2 mM VC) to balance gel for 30 min (keep the gel immersing in equilibrium liquid and replace the equilibrium liquid every other 10 min).

(6) After balancing, 100 mL of catalytic liquid (50 mM pH7.0 potassium phosphate buffer solution, containing 4 mM VC and 3 mM H$_2$O$_2$) was added to soak the protein gel for 30 min for enzymatic reaction (shaking slowly and kept the protein gel immersing in catalytic liquid).

(7) After enzymatic reaction, the gel was washed with 50 mM pH 7.0 potassium phosphate buffer solution for 1 min to remove the catalytic liquid.

(8) Finally, the protein gel was immersed in 100 mL coloration liquid (50 mM pH7.8 potassium phosphate, containing 28 mM MTEMED and 2.45 mM NBT) with slowly shaking for chromogenic reaction (the gel should be always immersed in coloration liquid). After 10-20 min, the reaction was terminated by adding sterile water and captured immediately.

Figure 2:
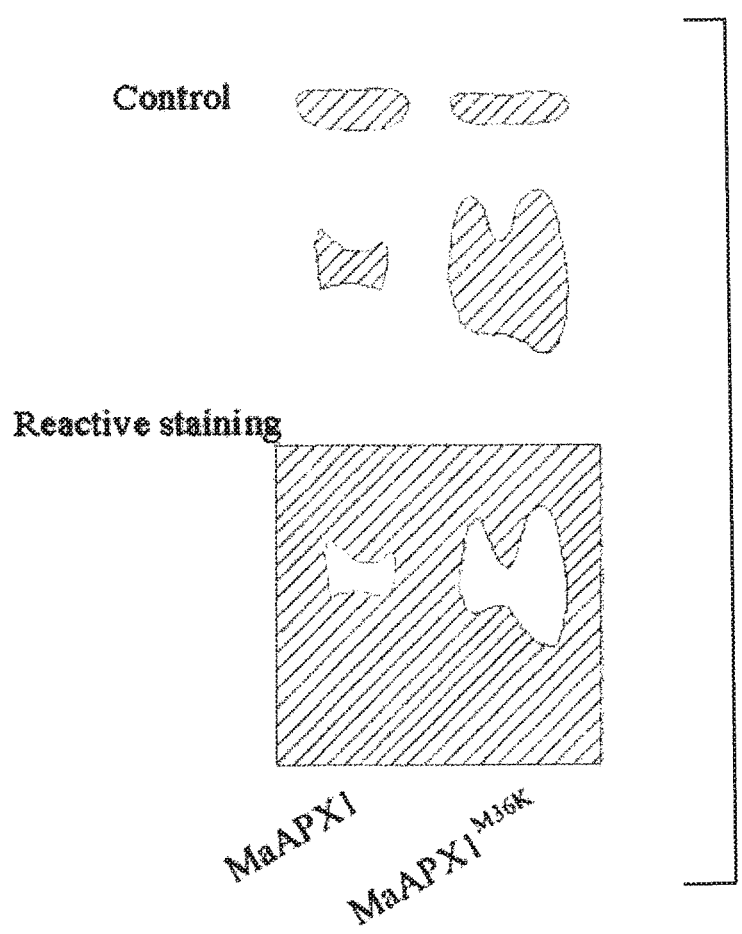
FIG. 2 is a comparison diagram showing protein activity measured by reactive staining in embodiments of the present invention.

(9) The whole experimental process should be kept in the dark from the step (5).The results were shown in FIG. 2.

The present invention provides an ascorbate peroxidase mutant MaAPX1$^{M36K}$ and application thereof. The mutant MaAPX1$^{M36K}$ reconstruction protein is expressed by prokaryotic. The results showed that the mutant MaAPX1$^{M36K}$ activity increased by nearly 5 times. It provides a technical reference for the further study of APX1.

As is mentioned above, it is only the preferred embodiment of the invention. It should be pointed out that for the ordinary technicians of the technical field, some improvements and modifications can be made without deviating from the principle of the invention. These improvements and modifications should also be considered as the protection scope of the invention.

What is claimed is:

1. A mutant of *Musa acuminata* ascorbate peroxidase 1 with a methionine at position 36 is mutated to lysine (MaAPX1$^{M36K}$), wherein the amino acid sequence of the mutant MaAPX1$^{M36K}$ is shown in SEQ ID NO: 3 having ascorbate peroxidase activity.

2. A method of using the mutant MaAPX1$^{M36K}$ of claim 1 in improving the activity of ascorbate peroxidase by changing a hydrophobicity in a center of the ascorbate peroxidase compared to non-mutant ascorbate peroxidase.

* * * * *

SEQUENCE LISTING

<160> NUMBER OF SEQ ID NOS: 7

<210> SEQ ID NO 1
<211> LENGTH: 750
<212> TYPE: DNA
<213> ORGANISM: Musa acuminata Lour.

<400> SEQUENCE: 1

```
atggcgaagt cgtatccgac ggtgagtgag gagtaccaga aggcggtaga gaaggccaag      60
aggaagctcc gtggcctcat cgccgagaag aactgtgccc cgttgatgct ccggctcgcg     120
tggcactcgg cgggtacgta cgatgtggtg tcaaagacgg gcggtccgtt cgggaccatg     180
aggttccctg cggagctcgc ccacgcgcc aacaacgggc tcaacatcgc tgtcaggctc      240
ttggagccca tcaaggagca gttccccatc ttgacatacg ctgacttcta tcagctcgcc     300
ggagttgtgg ctgtcgaagt taccggagga ccggagatcc ctttccatcc tgggagggag     360
gacaagcctg aacctcccgt agaaggtcgc cttcctgatg ctaccaaggg ttctgatcac     420
cttagggatg tgtttggtca catgggtctc agcgatcagg atatcgttgc attatctggt     480
ggacacacac tgggaaggtg ccacaaggag cgatctggtt ttgaggggc ttggacttcc      540 aatcctctta tttttgacaa ctcatacttc aaggaactcc tgagtggaga gaaagaagac     600
cttctccagc tgccttctga caaggccctt ctaactgatc ctgtattccg ccctcttgtg     660
gagaaatatg ctgccgatga ggatgccttc tttgctgatt acactgaagc tcacctgaag     720
ctctcagaac tcggatttgc tgaggcttaa                                      750
```

<210> SEQ ID NO 2
<211> LENGTH: 249
<212> TYPE: PRT
<213> ORGANISM: Musa acuminata Lour.

<400> SEQUENCE: 2

```
Met Ala Lys Ser Tyr Pro Thr Val Ser Glu Glu Tyr Gln Lys Ala Val
1               5                   10                  15

Glu Lys Ala Lys Arg Lys Leu Arg Gly Leu Ile Ala Glu Lys Asn Cys
            20                  25                  30

Ala Pro Leu Met Leu Arg Leu Ala Trp His Ser Ala Gly Thr Tyr Asp
        35                  40                  45

Val Val Ser Lys Thr Gly Gly Pro Phe Gly Thr Met Arg Phe Pro Ala
    50                  55                  60

Glu Leu Ala His Gly Ala Asn Asn Gly Leu Asn Ile Ala Val Arg Leu
65                  70                  75                  80

Leu Glu Pro Ile Lys Glu Gln Phe Pro Ile Leu Thr Tyr Ala Asp Phe
                85                  90                  95

Tyr Gln Leu Ala Gly Val Val Ala Val Glu Val Thr Gly Gly Pro Glu
            100                 105                 110

Ile Pro Phe His Pro Gly Arg Glu Asp Lys Pro Glu Pro Pro Val Glu
        115                 120                 125
```

```
Gly Arg Leu Pro Asp Ala Thr Lys Gly Ser Asp His Leu Arg Asp Val
    130                 135                 140

Phe Gly His Met Gly Leu Ser Asp Gln Asp Ile Val Ala Leu Ser Gly
145                 150                 155                 160

Gly His Thr Leu Gly Arg Cys His Lys Glu Arg Ser Gly Phe Glu Gly
                165                 170                 175

Ala Trp Thr Ser Asn Pro Leu Ile Phe Asp Asn Ser Tyr Phe Lys Glu
                180                 185                 190

Leu Leu Ser Gly Glu Lys Glu Asp Leu Leu Gln Leu Pro Ser Asp Lys
                195                 200                 205

Ala Leu Leu Thr Asp Pro Val Phe Arg Pro Leu Val Glu Lys Tyr Ala
        210                 215                 220

Ala Asp Glu Asp Ala Phe Phe Ala Asp Tyr Thr Glu Ala His Leu Lys
225                 230                 235                 240

Leu Ser Glu Leu Gly Phe Ala Glu Ala
                245
```

<210> SEQ ID NO 3
<211> LENGTH: 249
<212> TYPE: PRT
<213> ORGANISM: artificial sequence
<220> FEATURE:
<223> OTHER INFORMATION: an amino acid sequence of the mutant MaAPX1M36K

<400> SEQUENCE: 3

```
Met Ala Lys Ser Tyr Pro Thr Val Ser Glu Glu Tyr Gln Lys Ala Val
1               5                   10                  15

Glu Lys Ala Lys Arg Lys Leu Arg Gly Leu Ile Ala Glu Lys Asn Cys
                20                  25                  30

Ala Pro Leu Lys Leu Arg Leu Ala Trp His Ser Ala Gly Thr Tyr Asp
            35                  40                  45

Val Val Ser Lys Thr Gly Gly Pro Phe Gly Thr Met Arg Phe Pro Ala
        50                  55                  60

Glu Leu Ala His Gly Ala Asn Asn Gly Leu Asn Ile Ala Val Arg Leu
65                  70                  75                  80

Leu Glu Pro Ile Lys Glu Gln Phe Pro Ile Leu Thr Tyr Ala Asp Phe
                85                  90                  95

Tyr Gln Leu Ala Gly Val Val Ala Val Glu Val Thr Gly Gly Pro Glu
                100                 105                 110

Ile Pro Phe His Pro Gly Arg Glu Asp Lys Pro Glu Pro Pro Val Glu
            115                 120                 125

Gly Arg Leu Pro Asp Ala Thr Lys Gly Ser Asp His Leu Arg Asp Val
    130                 135                 140

Phe Gly His Met Gly Leu Ser Asp Gln Asp Ile Val Ala Leu Ser Gly
145                 150                 155                 160

Gly His Thr Leu Gly Arg Cys His Lys Glu Arg Ser Gly Phe Glu Gly
                165                 170                 175

Ala Trp Thr Ser Asn Pro Leu Ile Phe Asp Asn Ser Tyr Phe Lys Glu
                180                 185                 190

Leu Leu Ser Gly Glu Lys Glu Asp Leu Leu Gln Leu Pro Ser Asp Lys
                195                 200                 205

Ala Leu Leu Thr Asp Pro Val Phe Arg Pro Leu Val Glu Lys Tyr Ala
        210                 215                 220

Ala Asp Glu Asp Ala Phe Phe Ala Asp Tyr Thr Glu Ala His Leu Lys
225                 230                 235                 240
```

```
Leu Ser Glu Leu Gly Phe Ala Glu Ala
            245
```

<210> SEQ ID NO 4
<211> LENGTH: 40
<212> TYPE: DNA
<213> ORGANISM: artificial sequence
<220> FEATURE:
<223> OTHER INFORMATION: Forward primer of the primer containing the
      restriction site

<400> SEQUENCE: 4
ccgcgcggca gccatatggc gaagtcgtat ccgacggtga                    40

<210> SEQ ID NO 5
<211> LENGTH: 43
<212> TYPE: DNA
<213> ORGANISM: artificial sequence
<220> FEATURE:
<223> OTHER INFORMATION: Reverse primer of the primer containing the
      restriction site

<400> SEQUENCE: 5
agtcatgcta gccatatgtt aagcctcagc aaatccgagt tct                43

<210> SEQ ID NO 6
<211> LENGTH: 27
<212> TYPE: DNA
<213> ORGANISM: artificial sequence
<220> FEATURE:
<223> OTHER INFORMATION: Forward primer of the primer containing the
      mutation site

<400> SEQUENCE: 6
aactgtgccc cgttgaagct ccggctc                                  27

<210> SEQ ID NO 7
<211> LENGTH: 27
<212> TYPE: DNA
<213> ORGANISM: artificial sequence
<220> FEATURE:
<223> OTHER INFORMATION: Reverse primer of the primer containing the
      mutation site

<400> SEQUENCE: 7
gagccggagc ttcaacgggg cacagtt                                  27